US010585076B2

(12) United States Patent
Goto et al.

(10) Patent No.: US 10,585,076 B2
(45) Date of Patent: Mar. 10, 2020

(54) GAS-LIQUID SEPARATOR AND SUPER-CRITICAL FLUID DEVICE

(71) Applicant: SHIMADZU CORPORATION, Kyoto-shi, Kyoto (JP)

(72) Inventors: Hiroomi Goto, Kyoto (JP); Risa Kajiyama, Kyoto (JP); Takahiro Mori, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 513 days.

(21) Appl. No.: 15/510,740

(22) PCT Filed: Sep. 17, 2014

(86) PCT No.: PCT/JP2014/074539
§ 371 (c)(1),
(2) Date: Mar. 13, 2017

(87) PCT Pub. No.: WO2016/042618
PCT Pub. Date: Mar. 24, 2016

(65) Prior Publication Data
US 2017/0276654 A1 Sep. 28, 2017

(51) Int. Cl.
B01D 53/02 (2006.01)
G01N 30/80 (2006.01)
(Continued)

(52) U.S. Cl.
CPC .............. *G01N 30/80* (2013.01); *B01D 19/00* (2013.01); *B01D 19/0005* (2013.01);
(Continued)

(58) Field of Classification Search
CPC .... B01D 15/40; B01D 19/00; B01D 19/0005; B01D 19/0042; G01N 1/4055;
(Continued)

(56) References Cited

U.S. PATENT DOCUMENTS

2002/0144949 A1* 10/2002 Berger ............... B01D 11/0203
210/656
2003/0019812 A1* 1/2003 Berger ............... B01D 11/0203
210/656
(Continued)

FOREIGN PATENT DOCUMENTS

CN 102091441 A 6/2011
JP 63-221812 A 9/1988
(Continued)

OTHER PUBLICATIONS

International Search Report for PCT/JP2014/074539 dated May 19, 2015 [PCT/ISA/210].
(Continued)

*Primary Examiner* — Christopher P Jones
(74) *Attorney, Agent, or Firm* — Sughrue Mion, PLLC

(57) ABSTRACT

A gas-liquid separator according to an embodiment of the present invention separates a mobile phase containing a gas and a liquid into a gas and a liquid. The gas-liquid separator according to the embodiment of the present invention includes an introduction flow channel to which a mobile phase is introduced, and a plurality of discharge flow channels connected to the introduction flow channel. A gas and a liquid are discharged from a discharge port of the discharge flow channel.

10 Claims, 16 Drawing Sheets

(51) Int. Cl.
    *B01D 19/00*     (2006.01)
    *G01N 30/02*     (2006.01)
    *G01N 1/40*     (2006.01)
    *B01D 15/40*     (2006.01)
    *G01N 35/10*     (2006.01)

(52) U.S. Cl.
    CPC ....... *B01D 19/0042* (2013.01); *G01N 1/4055* (2013.01); *G01N 30/02* (2013.01); *B01D 15/40* (2013.01); *G01N 35/109* (2013.01); *G01N 2001/4061* (2013.01)

(58) Field of Classification Search
    CPC ........... G01N 2001/4061; G01N 30/02; G01N 30/80; G01N 35/109
    See application file for complete search history.

(56) References Cited

U.S. PATENT DOCUMENTS

| | | |
|---|---|---|
| 2010/0038299 A1 | 2/2010 | Matabe |
| 2010/0077874 A1* | 4/2010 | Kanomata .......... B01D 11/0203 73/863.21 |
| 2015/0330954 A1 | 11/2015 | Goto et al. |

FOREIGN PATENT DOCUMENTS

| | | |
|---|---|---|
| JP | 05-066220 A | 3/1993 |
| JP | 2000-320933 A | 11/2000 |
| JP | 2005-195398 A | 7/2005 |
| JP | 2007-120972 A | 5/2007 |
| WO | 2014/083639 A1 | 6/2014 |

OTHER PUBLICATIONS

Written Opinion for PCT/JP2014/074539 dated May 19, 2015 [PCT/ISA/237].

Communication dated Jul. 2, 2018, from the State Intellectual Property Office of People's Republic of China in counterpart Application No. 201480081676.6.

* cited by examiner

Time

GAS-LIQUID SEPARATOR AND SUPER-CRITICAL FLUID DEVICE

CROSS REFERENCE TO RELATED APPLICATIONS

This application is a National Stage of International Application No. PCT/JP2014/074539 filed Sep. 17, 2014, the contents of all of which are incorporated herein by reference in their entirety.

TECHNICAL FIELD

The present invention relates to a gas-liquid separator and a super-critical fluid device.

BACKGROUND ART

In a super-critical fluid chromatography (SFC) device or a super-critical fluid extraction (SFE) device, a super-critical fluid of over 10 MPa (megapascals), or $CO_2$ in a liquid state is decompressed to atmospheric pressure and vaporized after passing through a back pressure regulator (BPR). In a SFC and a SFE each having a dispensing function, a sample dissolved in, for example, a mixed fluid of $CO_2$ and a modifier, is collected after being passed through a BPR. Since the vaporized $CO_2$ has a volume expanded as many as 400 times, a problem occurs that a fluid flowing out from outlet piping scatters to lose the sample.

In order to solve the problem, a gas-liquid separator is required which separates a gas ($CO_2$) and a liquid (modifier, mainly MeOH) and recovers only a liquid. Such a gas-liquid separator is disclosed in, for example, Patent Documents 1 to 7.

After passing through a column in a SFC or a SFE, targets to be dispensed emerge as a group of chromatograph peaks. Each peak of a group of chromatograph peaks is called a fraction. A large number of fractions (peaks) are adjacently separated with a space in, for example, seconds. The fractions should all be collected.

For the collection of fractions, a fraction collector is used. For example, a fraction collector used in ordinary liquid chromatograph (LC) drips numerous fractions into numerous collection vials spatially arranged (e.g. test tubes etc.) by moving a head with a discharge port in an X-Y direction.

Here, a fraction dispensing method will be described separately in, for example, three types.

A first dispensing method is a method in which gas-liquid separators are provided corresponding to a plurality of gathering vials. This method is disclosed in, for example, Patent Documents 1, 3, and 7. The numerous fractions have flow channels thereof switched by a valve so as to be led to the gathering vials via a gas-liquid separator. Through one gas-liquid separator, only one fraction passes. Accordingly, this method has an advantage that neither an amount of a dead volume nor cross-contamination (for example, individual peaks are broadened to cross with each other) causes a problem. However, commercially available switching valves, for example, have a maximum of six sides, and for dispensing more fractions (target chromatograph peaks to be dispensed), valves should be connected in a plurality of stages to involve problems of an increase in scale of a system and complication of the same.

A second dispensing method is a method of conducting gas-liquid separation within a collection vial. Since this method involves no dead volume, the method has an advantage of having no cross-contamination problem. This method is disclosed in, for example, Patent Document 2. The method disclosed in Patent Document 2 is capable of dispensing numerous fractions by moving a fraction discharging probe to numerous recovery vials spatially arranged similarly to a fraction collector for an LC, without using a switching valve. However, in the method disclosed in Patent Document 2, the recovery vial and a front end of the probe should be attached or detached by moving the front end of the probe in a Z-direction temporally before and after the probe is moved in an X-Y direction. Therefore, the method disclosed in Patent Document 2 is not allowed to dispense fractions during a dead time of attachment and detachment, and has accordingly difficulty in dispensing fractions extremely close to each other.

A third dispensing method is a type having one gas-liquid separator in a flow channel on an upstream side of a fraction collector. Since this method sends only a liquid to the fraction collector, the method is capable of dispensation as in a conventional LC. The method is disclosed in, for example, Patent Documents 4, 6, and 7.

For realizing a device capable of acquiring numerous fractions while ensuring simplicity of a device configuration, the above third dispensing method is considered to be preferable. However, when a tube with an enlarged internal diameter called a dripper is used as in Patent Document 4, a swirling flow is generated in the enlarged internal diameter portion of the tube as shown in Patent Document 5 to cause cross-contamination in which a plurality of fractions temporally close to each other mix with each other. When a swirling flow is generated in the tube, flows go vertically adjacent to each other between a first round and a second round, and between the second round and a third round. It is easily supposed that when numerous fractions come into such a flow, components temporally different from each other mix with each other. A swirling flow disclosed in Patent Document 6 and remains in a porous filter as disclosed in Patent Document 7 also cause cross-contamination.

Additionally, dead volumes in an inner tube as disclosed in Patent Document 4, in a chamber as disclosed in Patent Document 6, in a chamber as disclosed in Patent Document 7, and the like broaden a peak. This also causes cross-contamination. Additionally, a problem of carryover occurs in which a residual component mixes at subsequent dispensation. Such a structure as disclosed, for example, in Patent Document 4, is not preferable, in which a mobile phase passes through an inner wall of a chamber having a large capacity.

PRIOR ART DOCUMENTS

Patent Documents

Patent Document 1: Japanese Translation of PCT Publication No. 2009-5440422
Patent Document 2: Japanese Patent Laid-open Publication No. 2010-78532
Patent Document 3: Japanese Patent No. 4918641
Patent Document 4: Japanese Translation of PCT Publication No. 2012-508882
Patent Document 5: Japanese Translation of PCT Publication No. 2009-5440422
Patent Document 6: Specification of U.S. Patent Publication No. 2013/0180404

Patent Document 7: Brochure of International Publication No. 2012/167180

SUMMARY OF THE INVENTION

Problems to be Solved by the Invention

The problem of scattering of liquid components including a sample is caused mainly by an extremely high linear velocity of $CO_2$ which attains atmospheric pressure and is expanded in volume as many as 400 times. Because of an extremely high linear velocity, the liquid scatters in mist as the same phenomenon as spraying (hereinafter, referred to as a spraying phenomenon). The linear velocity is inversely proportional to across section of a pipe through which a fluid flows.

Thus, in order to suppress a linear velocity, an internal diameter of a tube is enlarged in Patent Documents 1 and 4. However, when all the fractions pass through one gas-liquid separator, a problem of cross-contamination due to a swirling flow or an unnecessary dead volume occurs.

Additionally, for preventing a problem of carryover, in which out of a dead volume, a sample scattered to a part, through which no fluid ordinarily flows, flows out at subsequent dispensation, cleaning for removing a residual sample is required. For example, when a mobile phase with a low flow rate of approximately 10 ml/min (milliliter per minute) is flown in piping having an internal diameter of 3 mm (millimeter) or more, a (wet) part in which a mobile phase passes and a part (not wet) in which no mobile phase passes are formed on an inner surface of the piping. A sample adhered to a non-wet part causes carryover.

An object of the present invention is to suppress a linear velocity of a fluid without causing cross-contamination and carryover at the time of separation of a mobile phase containing a gas and a liquid into a gas and a liquid.

Solutions to the Problems

A gas-liquid separator according to an embodiment of the present invention is a gas-liquid separator that separates a mobile phase containing a gas and a liquid into a gas and a liquid, and includes an introduction flow channel to which a mobile phase is introduced, and a plurality of discharge flow channels connected to the introduction flow channel, in which from a discharge port of the discharge flow channel, a gas and a liquid are discharged.

A super-critical fluid device according to an embodiment of the present invention includes a pump, a back pressure regulator, and the gas-liquid separator according to the embodiment of the present invention, in which a mobile phase containing a liquid and a super-critical fluid or a liquefied gas is fed by the pump, and a mobile phase having passed through the back pressure regulator is introduced into the gas-liquid separator.

Effects of the Invention

The gas-liquid separator and the super-critical fluid device according to the embodiment of the present invention enable a linear velocity of a fluid to be suppressed without causing cross-contamination and carryover at the time of separation of a mobile phase containing a gas and a liquid into a gas and a liquid.

EMBODIMENTS OF THE INVENTION

Figure 1:
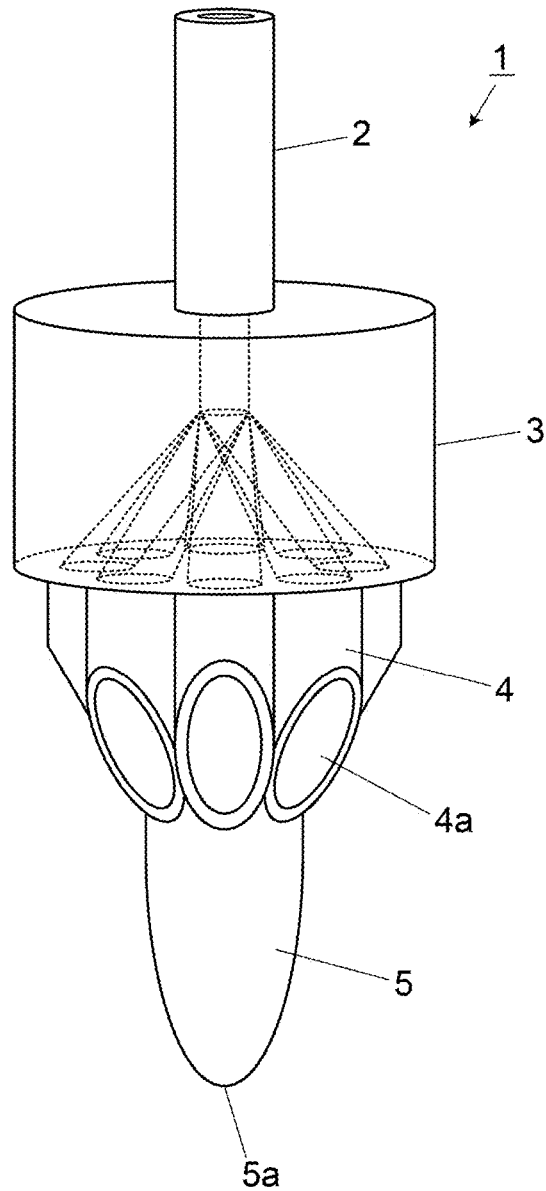
FIG. 1 is a schematic perspective view for explaining one embodiment of a gas-liquid separator.

A gas-liquid separator according to an embodiment of the present invention has an introduction flow channel branched into a plurality of discharge flow channels to increase a cross section of a flow. This enables the gas-liquid separator according to the embodiment of the present invention to suppress a linear velocity of a fluid without causing cross-contamination and carryover at the time of separation of a mobile phase containing a gas and a liquid into a gas and a liquid.

The mobile phase containing a gas and a liquid to be introduced into the gas-liquid separator according to the embodiment of the present invention includes a liquid and a super-critical fluid, or a super-critical fluid of a fluid including a liquefied gas, or a gas-liquid mixed fluid in which a part or the entire of a liquefied gas is vaporized.

Now, as disclosed in, for example, Patent Documents 4, 6, and 7, when a tube with an enlarged internal diameter is used as a gas-liquid separator, an optimum internal diameter of the tube with an enlarged internal diameter, taking problems of wetting and scattering into consideration, depends on a flow rate of a mobile phase. Accordingly, a problem occurs that an internal diameter of a tube with an enlarged internal diameter needs to be changed according to a flow rate of a mobile phase. Additionally, when one type of an internal diameter is adopted, a dynamic range for an applicable flow rate is small to invite a problem of a decrease in a sample recovery rate when a flow rate is changed.

Since an introduction flow channel is branched into a plurality of discharge flow channels to increase a cross section of a flow, the gas-liquid separator according to the embodiment of the present invention enables suppression of a linear velocity without reducing a dynamic range for an applicable flow rate. As compared with a tube with an enlarged internal diameter, the gas-liquid separator according to the embodiment of the present invention has a wider applicable flow rate range in which a high liquid recovery rate can be maintained.

The gas-liquid separator according to the embodiment of the present invention may further include, for example, a liquid collecting member having an outer wall surface on which a liquid discharged from a discharge port of the discharge flow channel moves while being adhered to the surface. Since in the gas-liquid separator of this embodiment, a liquid discharged from the discharge port of the discharge flow channel moves on the outer wall surface of the liquid collecting member, a dead volume is reduced. Since no unnecessary dead volume is present in the gas-liquid separator of the embodiment, cleaning is facilitated.

In the gas-liquid separator according to the embodiment of the present invention, a shape of an external appearance of the liquid collecting member has, for example, a cylindrical shape or a cone shape. However, a shape of an external appearance of the liquid collecting member is not limited to a cylindrical shape and a cone shape, but may be another shape.

Additionally, in the gas-liquid separator according to the embodiment of the present invention, for example, at least a part of the discharge flow channel may be formed within the liquid collecting member, and the discharge port of the discharge flow channel may be formed on the outer wall surface of the liquid collecting member.

In the gas-liquid separator according to the embodiment of the present invention, an internal diameter of the discharge flow channel may be, for example, 2 mm or less. However, the internal diameter of the discharge flow channel may be 2 mm or more as well.

In a super-critical fluid device according to the embodiment of the present invention, for example, a cooler may be connected between the back pressure regulator and the gas-liquid separator. Introduction of a mobile phase cooled by the cooler into the gas-liquid separator suppresses evaporation of a liquid after the mobile phase is subjected to gas-liquid separation, thereby increasing a recovery rate. However, the super-critical fluid device according to the embodiment of the present invention may not include the cooler.

The cooler has, for example, an orifice. By reducing an internal diameter of a flow channel, the orifice cools a mobile phase. Use of an orifice in the cooler enables a mobile phase to be cooled with a simple structure.

The super-critical fluid device according to the embodiment of the present invention may further include, for example, a sample injector connected between the pump and the back pressure regulator, a column connected between the sample injector and the back pressure regulator, and a detector connected between the column and the back pressure regulator. Since the gas-liquid separator according to the embodiment of the present invention can suppress cross-contamination and carryover, the super-critical fluid device according to the embodiment enables cross-contamination to be prevented, thereby allowing numerous adjacent fractions to be dispensable.

Further, the super-critical fluid device according to the embodiment of the present invention may include, for example, a temperature detector for detecting a temperature of a mobile phase immediately before being introduced into the gas-liquid separator, a temperature of the cooler or a temperature of the gas-liquid separator, and a control unit which causes the sample injector to operate upon determining that a result of monitoring of a temperature detected by the temperature detector becomes a specified value or below. Here, a temperature of a mobile phase immediately before being introduced into the gas-liquid separator represents a temperature of a mobile phase between the cooler and the gas-liquid separator.

With reference to the drawings, one embodiment of the present invention will be described.

Figure 2:
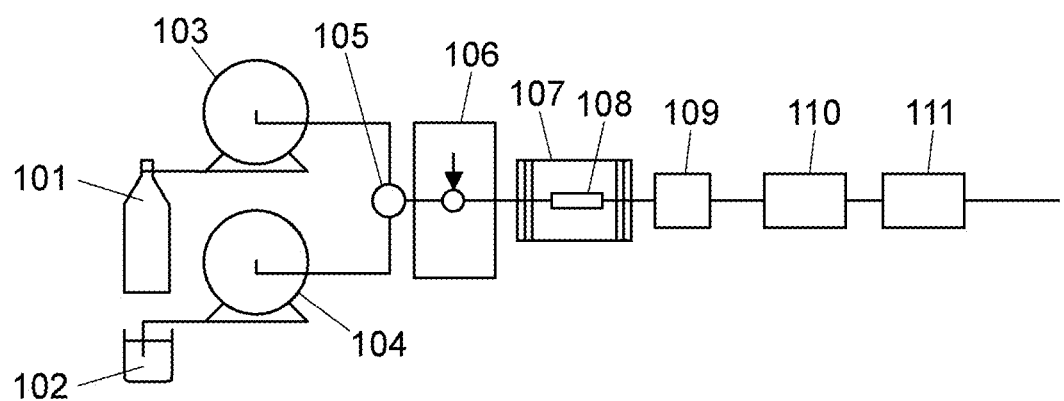
FIG. 2 is a schematic view of a configuration for explaining one embodiment of a super-critical fluid device.

FIG. 1 is a schematic perspective view for explaining one embodiment of the gas-liquid separator. FIG. 2 is a schematic view of a configuration for explaining one embodiment of the super-critical fluid device. First, with reference to FIG. 2, a configuration of the super-critical fluid device will be described.

The super-critical fluid device shown in FIG. 2 is a super-critical fluid chromatography device (SFC) including a gas-liquid separator. The SFC uses, as a mobile phase, for example, $CO_2$ which can attain a super-critical state at a relatively low temperature and low pressure. Additionally, with the mobile phase, a modifier (mainly MeOH) is mixed in order to increase a solubility of a measurement sample. Therefore, a liquid $CO_2$ obtained from a $CO_2$ cylinder 101 and a modifier 102 are fed by a $CO_2$ pump 103 and a modifier pump 104, respectively, and mixed by a mixer 105.

A fluid to which a sample is injected by an automatic sampler 106 (sample injector) passes through a column 108 disposed in a column oven 107. The sample is temporally separated. The temporally separated sample is detected by, for example, an ultraviolet (UV) detector 109.

A pressure of a flow channel arranged after the pump is maintained at a constant pressure not less than approximately 10 MPa by a pressure control valve 110 (back pressure regulator, BPR). After passing through the pressure control valve 110, the mobile phase is decompressed to the atmospheric pressure. Thereafter, on the basis of timing detected by the UV detector 109, desired components are recovered into gathering vials, respectively, by a fraction collector 111.

Figure 3:
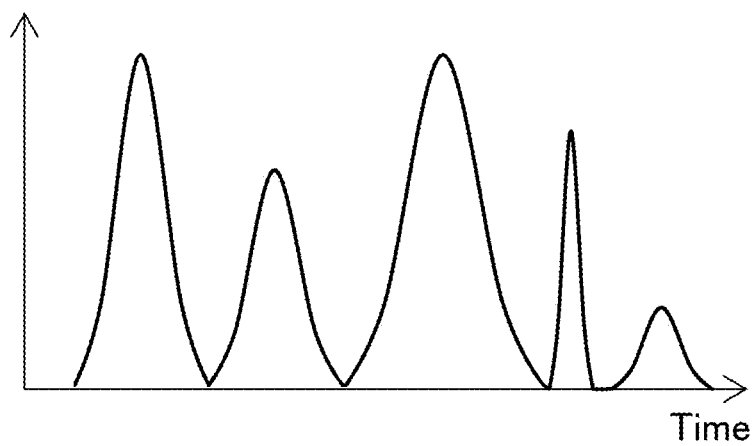
FIG. 3 is a diagram for explaining one example of a chromatograph peak having passed a column.

FIG. 3 is a diagram for explaining one example of a chromatograph peak having passed a column. In FIG. 3, the ordinate represents a peak intensity (arbitrary unit), and the abscissa represents time.

Shown in FIG. 3 is a group of chromatograph peaks as a target to be dispensed. Each one of these peaks is called a fraction. Numerous fractions (peaks) are adjacently separated with a space in seconds, for example. In a SFC, for example, these fractions should be all acquired.

From a piping outlet in the fraction collector 111, $CO_2$ having a volume expanded 400 times due to vaporization vigorously jets. In general, MeOH containing a sample scatters as a spraying phenomenon to decrease a sample recovery rate. The SFC of this embodiment includes a gas-liquid separator 1 as shown in FIG. 1 in a flow channel between the pressure control valve 110 and the fraction collector 111, or in the fraction collector 111, for improving the sample recovery rate.

The gas-liquid separator 1 will be described with reference to FIG. 1.

The gas-liquid separator 1 separates, for example, a mobile phase ($CO_2$+modifier) into a gas and a liquid. The gas-liquid separator 1 includes an inlet tube 2 (introduction flow channel), a flow channel branching member 3, a plurality of discharge flow channels 4, and a liquid inducing column 5 (liquid collecting member). Into the inlet tube 2, for example, a mobile phase containing $CO_2$ in a gas state and a modifier (liquid) is introduced. The plurality of discharge flow channels 4 is connected to the inlet tube 2 via the flow channel branching member 3.

Discharge ports 4a of the discharge flow channels 4 are arranged in contact with an outer wall surface of the liquid inducing column 5. The liquid inducing column 5 has a cylindrical shape. Liquid discharged from the discharge ports 4a of the discharge flow channels 4 is adhered to the outer wall surface of the liquid inducing column 5 and moved to a front end portion 5a.

The gas-liquid separator 1 branches a mobile phase flowing from the inlet tube 2 into the plurality of discharge flow channels 4 by passing the same through the flow channel branching member 3. An internal diameter of the discharge flow channel 4 is relatively small, for example, 2 mm or less. The gas-liquid separator 1 causes a modifier as a liquid discharged from the discharge ports 4a of the discharge flow channels 4 to move along the outer wall surface of the liquid inducing column 5 and to drip from the front end portion 5a of the liquid inducing column 5. When a linear velocity of the mobile phase is low enough, by making a liquid flow along a surface of a rod-shaped or flat member as shown in FIG. 1, the liquid can be dripped without scattering up to a certain flow rate.

Figure 4:
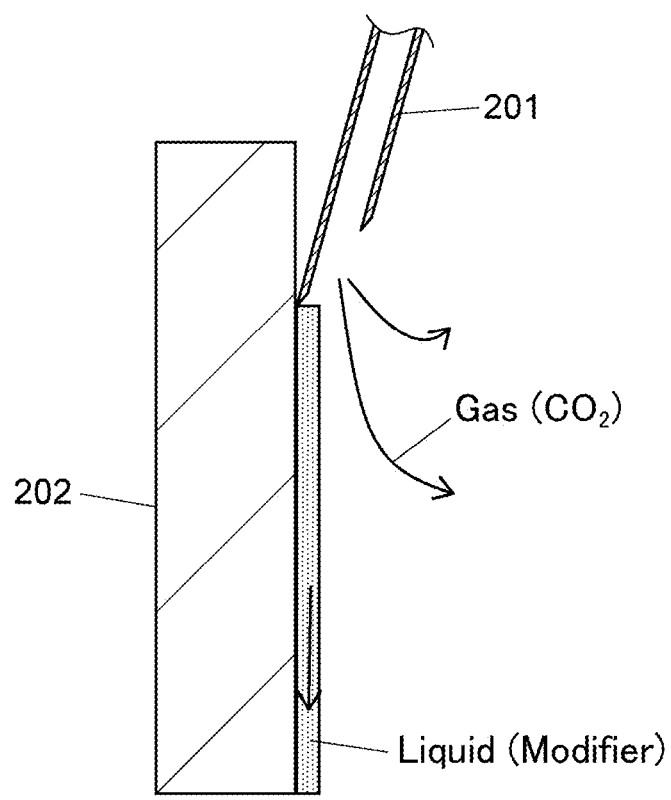
FIG. 4 is a view for explaining how a gas and a liquid discharged from piping flow.

FIG. 4 is a view for explaining how a gas and a liquid discharged from piping flow.

When a gas-liquid mixed fluid is discharged from a pipe 201, the liquid is caught by a wall surface of a wall 202 in contact with the pipe 201 by a phenomenon called the Coanda effect, and moves along the wall surface to flow. On the other hand, a gas is released to a free space irrespectively of the wall surface. This leads to execution of separation of a gas and a liquid.

Even in such a system as shown in FIG. 4, when a linear velocity of a fluid is extremely high, the liquid scatters under favor of a gas similarly to spraying. Accordingly, it is necessary to sufficiently decrease the linear velocity of the fluid.

For decreasing a linear velocity of a fluid, it is effective to increase a cross section on which a fluid flows. However, when an internal diameter of a tube is increased, the problem of cross-contamination due to a swirling flow as mentioned in the description of the above Patent Document 4 occurs.

Thus, in the gas-liquid separator 1 shown in FIG. 1, in order to increase a cross section of a flow in a state where no swirling flow is generated, the piping is branched into a plurality of pipes (the discharge flow channels 4) each with a relatively small internal diameter. It is also an advantageous characteristic of this embodiment that a fluid from the discharge ports 4a of the piping after being branched flows along the outer wall of the liquid inducing column 5.

When gas-liquid separation is conducted with the piping discharge port disposed along the wall surface, gas $CO_2$ which will have a volume expanded as many as 400 times should be released using a space wide enough to prevent a flow of a liquid from being affected, so that a gas-liquid separation chamber should be large enough.

However, when a liquid is made to flow along an inner wall of a chamber as disclosed in Patent Document 1 or Patent Document 4, the size of the chamber directly leads to a dead volume of a flow channel to cause the problem of cross-contamination due to a broadened peak.

Thus, the gas-liquid separator 1 shown in FIG. 1 is designed to make a liquid flow along the outer wall of the liquid inducing column 5. As a result, even when a chamber, which is arranged so as to cover the gas-liquid separator 1, is formed to be large enough, the chamber invites no dead volume of a flow.

Another summary will be made for points of the principle of the above-described gas-liquid separation.

(1) Based on the Coanda effect, when a piping outlet is disposed along a wall surface, only a liquid flows on the wall surface to realize gas-liquid separation.

(2) However, when a linear velocity of a fluid is high, the liquid is sprayed under favor of a gas and is scattered to be lost.

(3) In order to suppress a linear velocity of a fluid, it is effective to increase a cross section of a flow.

(4) However, when an internal diameter of a tube is increased in order to increase a cross section of a flow, a swirling flow causes the problem of cross-contamination.

(5) For the purpose of expanding a cross section of a flow without generating a swirling flow, piping is branched into a plurality of pipes each having a relatively small internal diameter.

(6) Making discharge ports of the plurality of branched pipes be disposed along an outer wall of a column reduces a substantial dead volume of a flow channel.

Next, description will be made of a result of a linear velocity at which scattering of a liquid due to a spraying phenomenon can be suppressed, the linear velocity being estimated on the basis of experiment. Here, it has been verified that for suppressing a linear velocity to an extent not to reduce a recovery rate relative to a certain flow rate, what level of an internal diameter a pipe should have, and how many branched pipes should be used.

Figure 5:
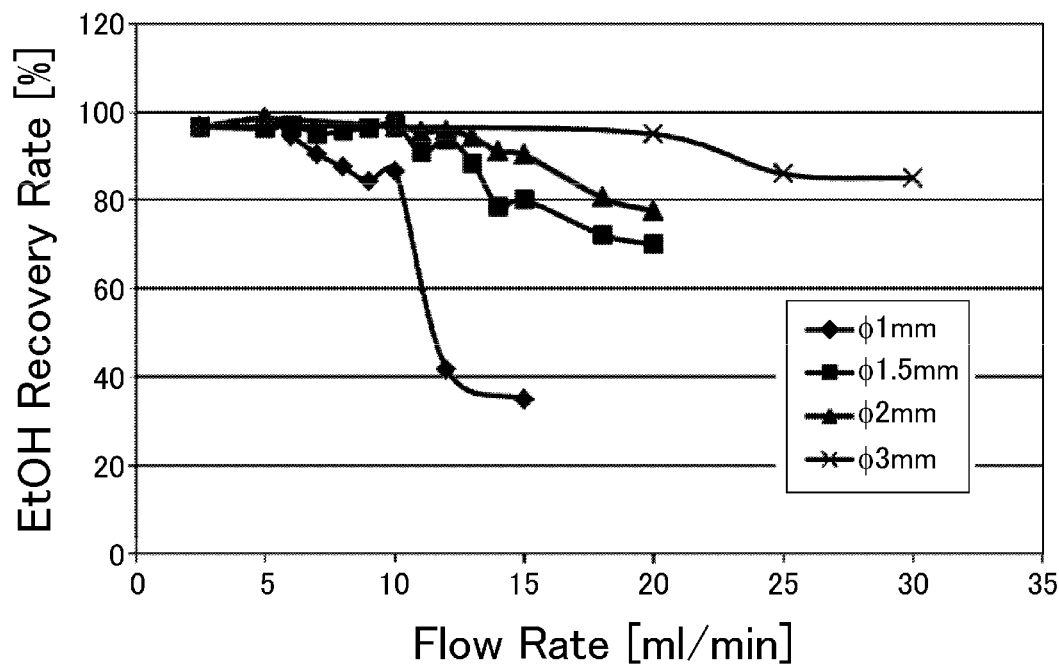
FIG. 5 is a diagram showing a result obtained by experiment of recovering a liquid, with a relatively narrow tube having an internal diameter of 3 mm or less provided along a wall surface.

FIG. 5 is a diagram showing a result obtained by experiment of recovering a liquid, with a relatively narrow tube having an internal diameter of 3 mm or less provided along a wall surface. In the graph of FIG. 5, the abscissa represents a flow rate and the ordinate represents an EtOH recovery rate.

For the respective internal diameters of a tube (100 1 mm, φ1.5 mm, φ2 mm, and φ0 mm), a high recovery rate was obtained up to a certain threshold flow rate. Then, over a certain threshold flow rate, the recovery rate is reduced with an increase in the flow rate.

With φ1.5 mm, for example, the liquid can be recovered without scattering up to the flow rate of 10 ml/min (the linear velocity is low enough). However, more than that flow rate, the recovery rate is reduced. In other words, with only one discharge flow channel, no high recovery rate is expected in a flow rate region as large as from 10 to 150 ml/min required for a preparative SFC. Thus, an introduction flow channel to which a mobile phase is introduced is branched into a plurality of discharge flow channels to reduce a flow rate (to reduce a linear velocity) per one discharge flow channel, thereby coping with a high flow rate.

Here, description will be made of another benefit of branching the piping into a plurality of pipes each with a small internal diameter. Pipes each with a small internal diameter have advantages with respect to a low flow rate. Even at a low flow rate such as 0.1 ml/min, for example, a gas-liquid mixed fluid passes in a tube while wetting an entire inner surface of the tube.

Figure 6:
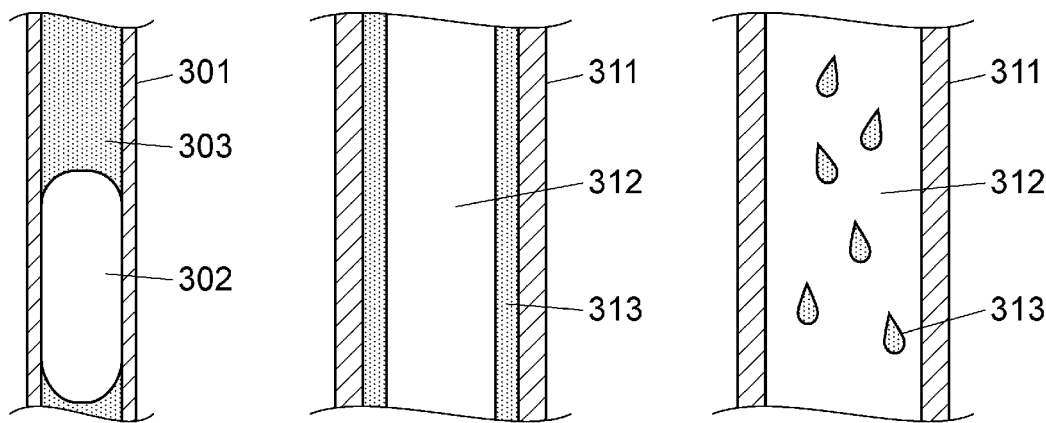
FIGS. 6(A), 6(B), and 6(C) are views for explaining how a gas-liquid mixed fluid flows in a tube having a small internal diameter and in a tube having a large internal diameter.

FIG. 6 is a view for explaining how a gas-liquid mixed fluid flows in a tube having a small internal diameter and in a tube having a large internal diameter.

In a tube 301 with a relatively small internal diameter shown in FIG. 6(a), a liquid 303 flows so as to wet an entire inner wall of the tube due to surface tension of the liquid and a gas 302 flows as a bubble.

A tube 311 shown in FIG. 6(b) and FIG. 6(c) is a tube having a relatively large internal diameter. As shown in FIG. 6(b), when the flow rate is high, a gas 312 with a low viscosity flows through a central part of the tube 311, and a liquid 313 flows so as to wet an entire inner wall of the tube 311. However, as shown in FIG. 6(c), when the flow rate is low, the liquid 313 is atomized, so that the liquid flows on only a part of the inner wall of the tube 311.

Therefore, in a case where a tube having a relatively large internal diameter is used as in Patent Document 1 or Patent Document 4, when a flow rate is low, a sample is adhered to an inner wall of a gas-liquid separator to cause contamination. Additionally, when the sample is replaced by another, a phenomenon occurs that the previous sample which remains elutes, the so-called problem of carryover.

As described in the foregoing, when a dynamic range of a tube having a diameter of 1.5 mm as an internal diameter is assumed to be 0.1 to 10 ml/min, use of, for example, 15 tubes realizes a gas-liquid separator with a dynamic range of 1.5 to 150 ml/min.

Figure 7:
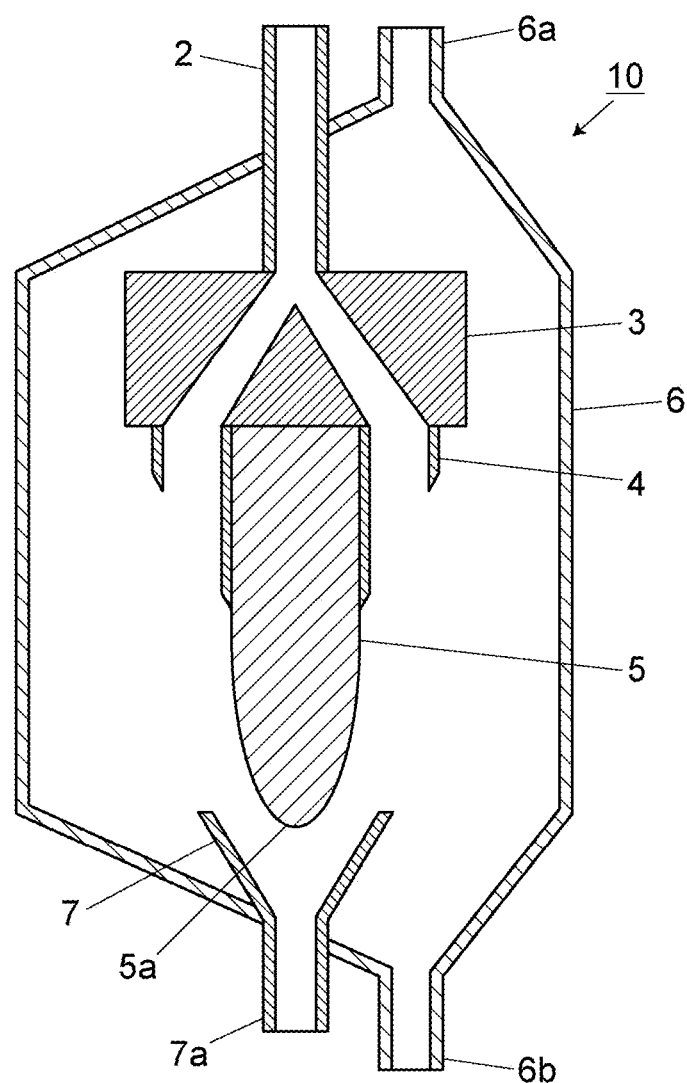
FIG. 7 is a schematic sectional view for explaining another embodiment of a gas-liquid separator.

FIG. 7 is a schematic sectional view for explaining another embodiment of a gas-liquid separator.

A gas-liquid separator 10 is disposed, for example, an upstream side of a fraction collector. The gas-liquid separator 10 includes a chamber 6 which houses the gas-liquid separator having the inlet tube 2, the flow channel branching member 3, the plurality of discharge flow channels 4, and the liquid inducing column 5 shown in FIG. 1. In the gas-liquid separator 10, the inside of the chamber 6 is pressurized to, for example, several atmospheric pressures, to obtain a driving force for feeding a liquid to the fraction collector.

A liquid dripped from the front end portion 5a of the liquid inducing column 5 of the gas-liquid separation device is recovered by a receiving port 7 and fed from a liquid outlet 8 to the fraction collector. Vaporized $CO_2$ fills the chamber 6 and is discharged from a $CO_2$ discharge port 6a. The chamber 6 is also provided with a waste fluid port 6b for cleaning. The gas-liquid separator 10 is arranged, for example, on the flow channel between the pressure control valve 110 and the fraction collector 111 in the SFC shown in FIG. 1.

Here, the gas-liquid separator 10 is characterized in that unlike conventional art, no sample fluid passes on an inner wall of the chamber 6 in which gas-liquid separation is conducted. Accordingly, the size itself of the chamber 6 does not lead to a dead volume. In other words, even when the chamber 6 is increased in size in order not to hinder a flow of a large amount of vaporized $CO_2$, a liquid containing a sample passes only along the outer wall of the liquid inducing column 5. In this case, the dead volume corresponds not to a volumetric capacity of any structure but to a volume of a liquid flowing along the liquid inducing column 5. Accordingly, a dead volume is extremely reduced to avoid the above-described problem of cross-contamination. Additionally, even if the sample scatters under favor of gas $CO_2$ and is adhered to the inner wall of the chamber 6, the adhered sample is only discharged from the waste fluid port 6b at the time of cleaning, and no carryover occurs in subsequent dispensation.

Figure 8:
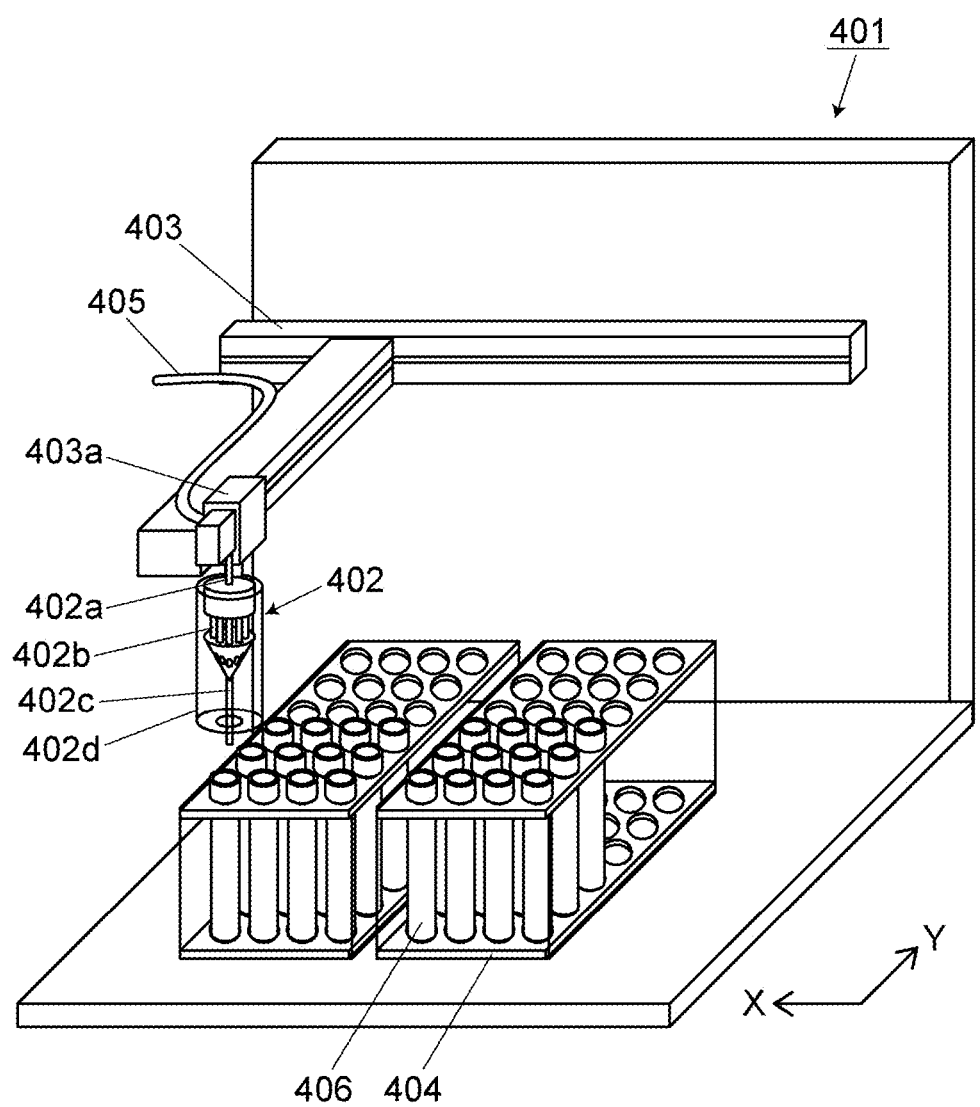
FIG. 8 is a schematic perspective view for explaining one example of a fraction collector including the gas-liquid separator according to the embodiment.

FIG. 8 is a schematic perspective view for explaining one example of a fraction collector including the gas-liquid separator according to the embodiment.

A fraction collector 401 includes a gas-liquid separator 402, an X-Y stage 403, and a collection vial holding unit 404.

The gas-liquid separator 402 includes an inlet tube 402a (introduction flow channel), a plurality of discharge flow channels 402b, a liquid inducing block and a liquid inducing column 402c (liquid collecting member), and a cover 402d. To the inlet tube 402a, a mobile phase is introduced. The plurality of discharge flow channels 402b is connected to the inlet tube 402a. The discharge ports 4a of the discharge flow channels 402b are arranged in contact with an outer wall surface of the liquid inducing block and the liquid inducing column 402c. The cover 402d is arranged around the discharge flow channels 402b, and the liquid inducing block and the liquid inducing column 402c.

The X-Y stage 403 moves a discharge head 403a in an X-Y direction. To the discharge head 403a, the gas-liquid separator 402 and a transfer tube 405 are connected. In the collection vial holding unit 404, a plurality of collection vials 406 is disposed. The fraction collector 401 is used, for example, as the fraction collector 111 in the SFC shown in FIG. 1.

A mobile phase fed from the transfer tube 405 to the gas-liquid separator 402 via the discharge head 403a is subjected to gas-liquid separation by the gas-liquid separator 402. The separated liquid is dripped from the liquid inducing block and the liquid inducing column 402c of the gas-liquid separator 402 to the collection vials 406. The gas-liquid separator of the embodiment is realized in a small size, for example, on the order of several centimeters. Accordingly, the gas-liquid separator 402 can be disposed at the discharge head 403a of the fraction collector 401.

Figure 9:
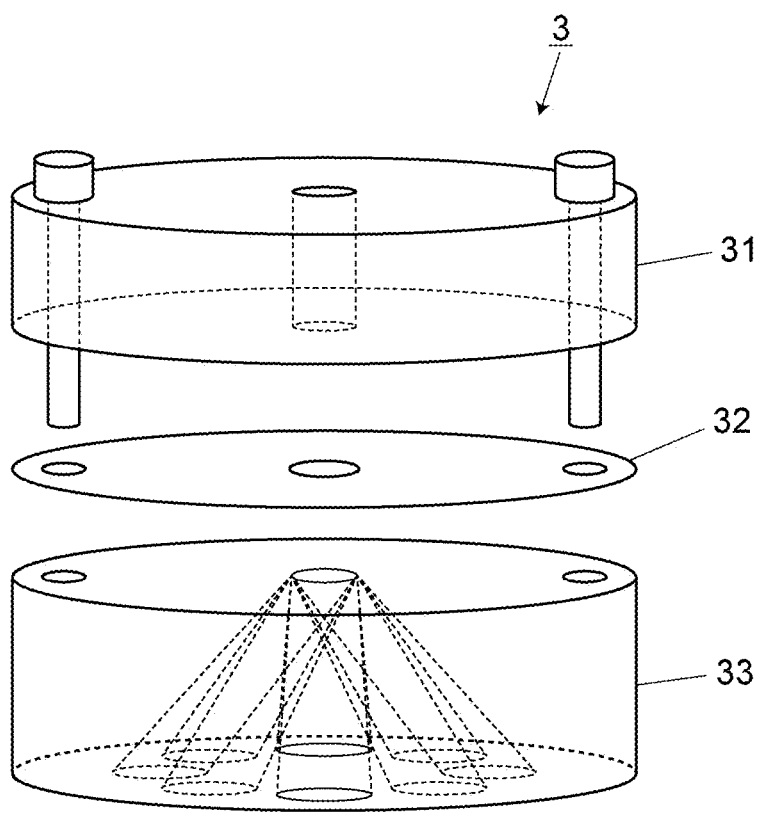
FIG. 9 is a schematic exploded perspective view for explaining one example of a structure of a flow channel branching member in the gas-liquid separator.

FIG. 9 is a schematic exploded perspective view for explaining one example of a structure of the flow channel branching member in the gas-liquid separator.

The flow channel branching member 3 includes, for example, a fluid introducing member 31, a sealing member 32, and a branching member 33.

The fluid introducing member 31 has a through hole with a diameter of approximately 1 mm at the center thereof. The sealing member 32, similarly to the fluid introducing member 31, has a through hole with a diameter of approximately 1 mm at the center thereof. A thickness of the sealing member 32 is, for example, approximately 0.2 mm. The branching member 33 includes one hole having a diameter of approximately 1 mm and provided at the center of a top surface thereof, and a plurality of holes provided on a bottom surface thereof. The hole of the top surface and the hole of the bottom surface communicate with each other. The fluid introducing member 31, the sealing member 32 and the branching member 33 are fastened by screws.

Materials of the fluid introducing member 31 and the branching member 33 are preferably, for example, SUS316 or PEEK in view of chemical resistance and sealability. A material of the sealing member 32 is preferably softer than the materials of the fluid introducing member 31 and the branching member 33 such as, for example, ultra-high polymer polyethylene, Kalrez (registered trademark), and the like.

Figure 10:
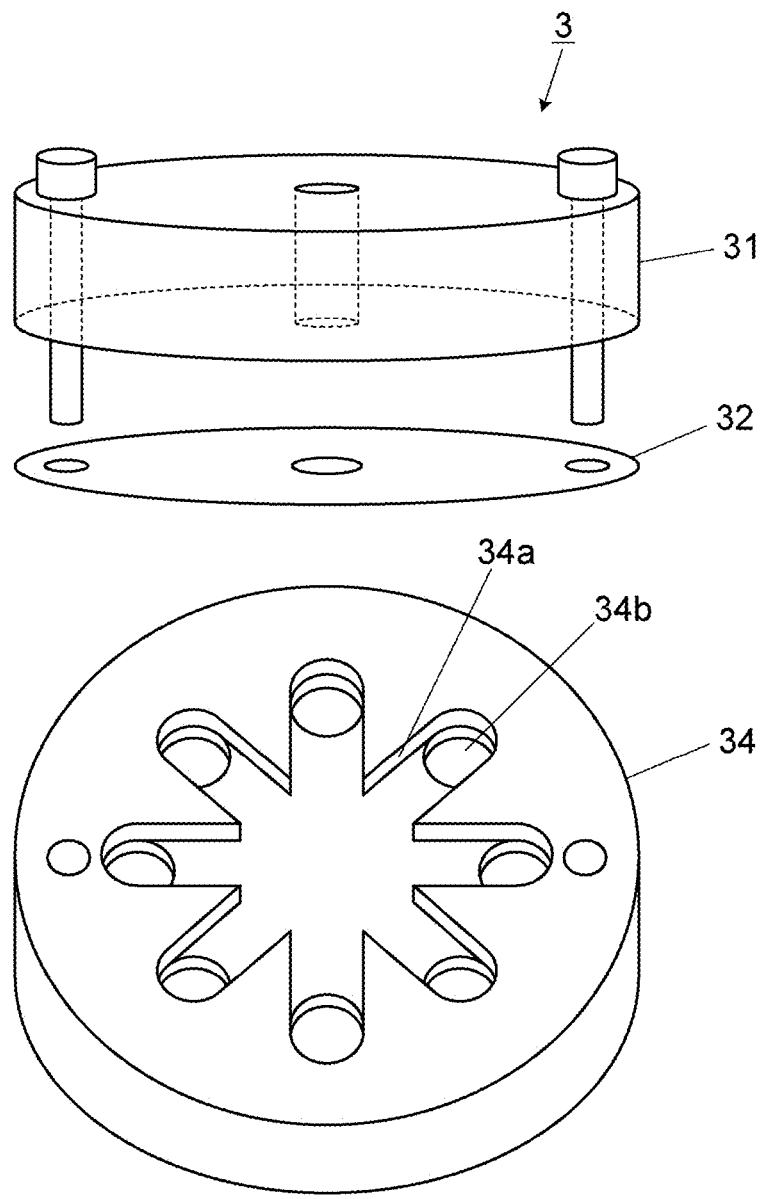
FIG. 10 is a schematic exploded perspective view for explaining another example of a structure of a flow channel branching member in the gas-liquid separator.

FIG. 10 is a schematic exploded perspective view for explaining another example of a structure of the flow channel branching member in the gas-liquid separator.

The flow channel branching member 3 shown in FIG. 10 includes a branching member 34 in place of the branching member 33 of the flow channel branching member 3 shown in FIG. 9.

The branching member 34 includes not a hole formed slantly as the branching member 33 but a branching flow channel formed with a groove 34a formed in a plane direction and with a through hole provided in an end portion of the groove. As compared with the branching member 33, the branching member 34 has a smaller dead volume. Additionally, the branching member 34 is capable of vertically connecting pipes of the discharge flow channel. The branching member 34 enables reduction in a length of the pipe to be connected of the discharge flow channel, and further enables reduction in a dead volume. On the other hand, in a case where the groove 34a of the branching member 34 is formed to have a uniform depth, and the groove 34a has a level bottom surface, particularly when a flow rate is extremely low, stay might arouse concerns about an expansion of a chromatograph peak and cross-contamination.

Figure 11:
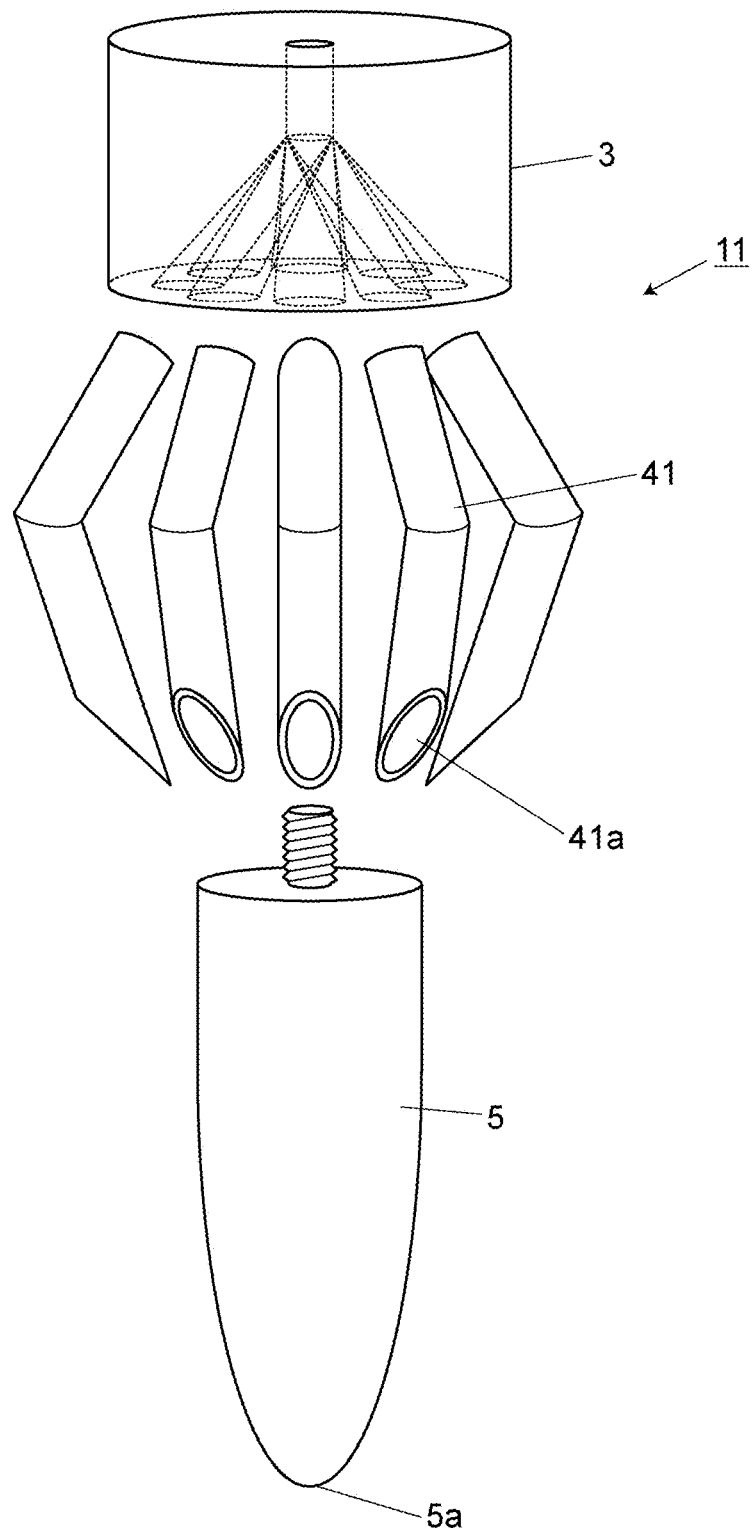
FIG. 11 is a schematic exploded perspective view for explaining a structure according to another embodiment of the gas-liquid separator.

FIG. 11 is a schematic exploded perspective view for explaining a structure according to another embodiment of the gas-liquid separator.

A gas-liquid separator 11 includes an introduction flow channel (illustration omitted), a flow channel branching member 3, a plurality of discharge flow channels 41, and a liquid inducing column 5. Structures of the introduction flow channel, the flow channel branching member 3, and the liquid inducing column 5 are the same as those of the gas-liquid separator 11 shown in FIG. 1. Although in FIG. 11, the flow channel branching member 3 is integrally shown, a specific structure thereof is, for example, the structure shown in FIG. 9 or FIG. 10.

In the gas-liquid separator 11, pipes of the plurality of discharge flow channels 41 are connected to the flow channel branching member 3. A discharge port 41a of the discharge flow channel 41 is in contact with an outer wall of the liquid inducing column 5. The optimum number of discharge flow channels 41 is determined depending on an internal diameter of the discharge flow channel 41. For example, on a basis of a result of the experiment shown in FIG. 5, 15 discharge flow channels 41 each with an internal diameter of 1.5 mm are connected. Although not shown in FIG. 11, connection between the flow channel branching member 3 and the plurality of discharge flow channels 41 is made by, for example, a ferrule and a male nut for use in common fastening of pipes.

When a length from a front end of the discharge port 41a of the discharge flow channel 41 to a front end portion 5a of the liquid inducing column 5 is too short, a liquid is not satisfactorily separated from a gas flow. Thus, it is preferable that 50 mm or more of a length is ensured from the front end of the discharge port 41a to the front end portion 5a of the liquid inducing column 5.

Additionally, with respect to the front end of the discharge port 41a of the discharge flow channel 41, when adjacent discharge flow channels 41 are brought to be too close, a discharged liquid flows through a space therebetween back to an upper side due to a capillary phenomenon, so that cross-contamination might occur. To avoid such a problem, it is preferable that a space of approximately 2 mm or more is ensured between the adjacent discharge ports 41a.

Figure 12:
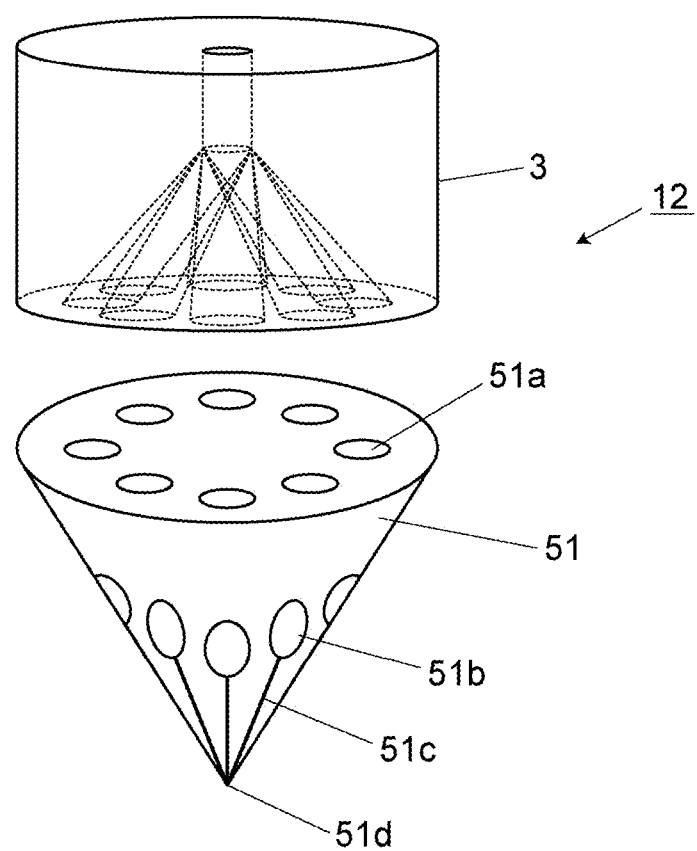
FIG. 12 is a schematic exploded perspective view for explaining a structure according to a further embodiment of the gas-liquid separator.

FIG. 12 is a schematic exploded perspective view for explaining a structure according to a further embodiment of the gas-liquid separator.

A gas-liquid separator 12 includes an introduction flow channel (illustration omitted), a flow channel branching member 3, and a liquid collecting member 51. Structures of the introduction flow channel and the flow channel branching member 3 are the same as those of the gas-liquid separator 11 shown in FIG. 10.

The liquid collecting member 51 is formed, for example, of a cone-shaped block. Inside the liquid collecting member 51, a discharge flow channel 51a configured with a through hole is formed. A discharge port 51b of the discharge flow channel 51a is arranged on a side wall surface (outer wall surface) of the liquid collecting member 51. On the side wall surface of the liquid collecting member 51, a groove 51c is formed at a position between the discharge port 51b and a front end portion 51d. A liquid discharged from the discharge port 51b of the discharge flow channel 51a is adhered to the side wall surface of the liquid collecting member 51 to move to the side of the front end portion 51d and drip from the front end portion 51d. It is noted that the groove 51c is not necessarily formed.

As compared with the gas-liquid separator 11 shown in FIG. 11, the gas-liquid separator 12 including the liquid collecting member 51 enables the number of parts to be more drastically reduced. Additionally, the gas-liquid separator 12 needs no consideration of the above-described space between adjacent discharge ports. Accordingly, an interval between the adjacent discharge ports 51b can be reduced to enable an outer diameter of the liquid collecting member 51 to be small, and thus, allow the gas-liquid separator 12 to be compact.

Additionally, the groove 51c prevents a stray flow of a liquid. The arrangement of the groove 51c is useful especially when a flow rate of a liquid is low.

For sealing a portion between the flow channel branching member 3 and the liquid collecting member 51, it is preferable that such a sheet as formed of ultra-high polymer polyethylene or Kalrez (registered trademark) is sandwiched between the flow channel branching member 3 and the liquid collecting member 51, though not shown.

Figure 13:
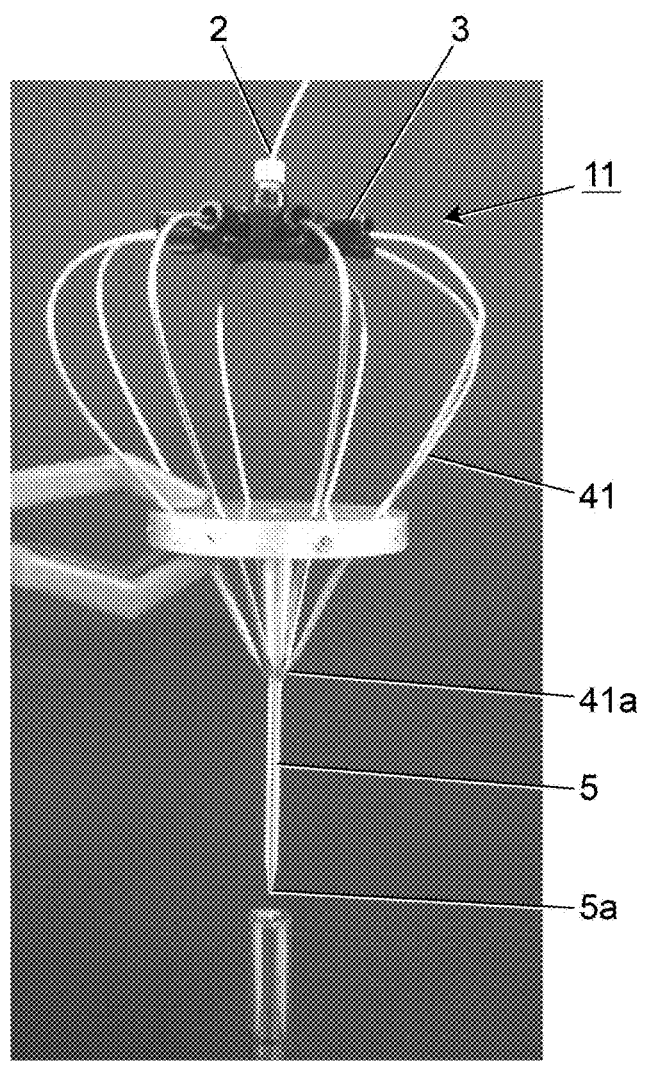
FIG. 13 illustrates an image showing a gas-liquid separator actually test-manufactured on the basis of a mechanism shown in FIG. 11.
Figure 14:
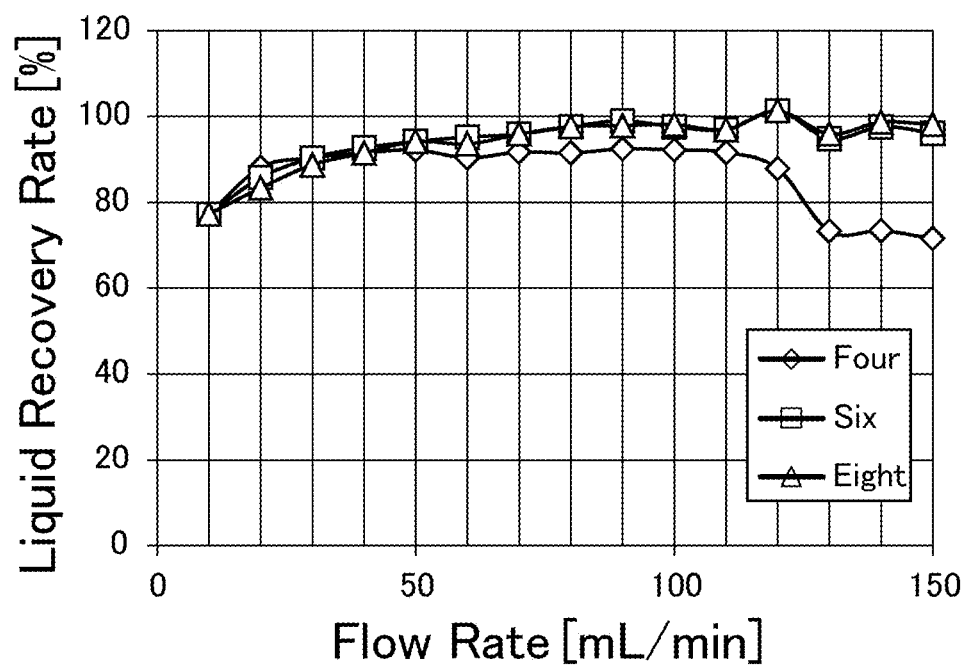
FIG. 14 is a diagram showing a result obtained by evaluating a liquid recovery rate after gas-liquid separation is conducted using the gas-liquid separator shown in FIG. 13.

FIG. 13 illustrates an image showing a gas-liquid separator actually test-manufactured on the basis of the mechanisms shown in FIG. 11. FIG. 14 is a diagram showing a result obtained by evaluating a liquid recovery rate after gas-liquid separation is conducted using the gas-liquid separator shown in FIG. 13. In FIG. 14, the ordinate represents a liquid recovery rate and the abscissa represents a flow rate of a mobile phase in an introduction flow channel. Internal diameters of pipes of the introduction flow channel and a branching flow channel are 1.5 mm. A discharge port of each pipe of the branching flow channel is cut at 10°. Evaluation was made of a liquid recovery rate at a flow rate of 10 to 150 ml/min when the number of branched pipes was four, six, and eight.

With six or more branches, a gas and a liquid were separated also at a high flow rate of 150 ml/min to obtain a liquid recovery rate of 95% or more. Additionally, it is found that at a flow rate of 40 ml/min or less, a liquid recovery rate was reduced. This is derived from roughness from an inner surface of piping used, and is not an inherent characteristic of a gas-liquid separator.

Figure 15:
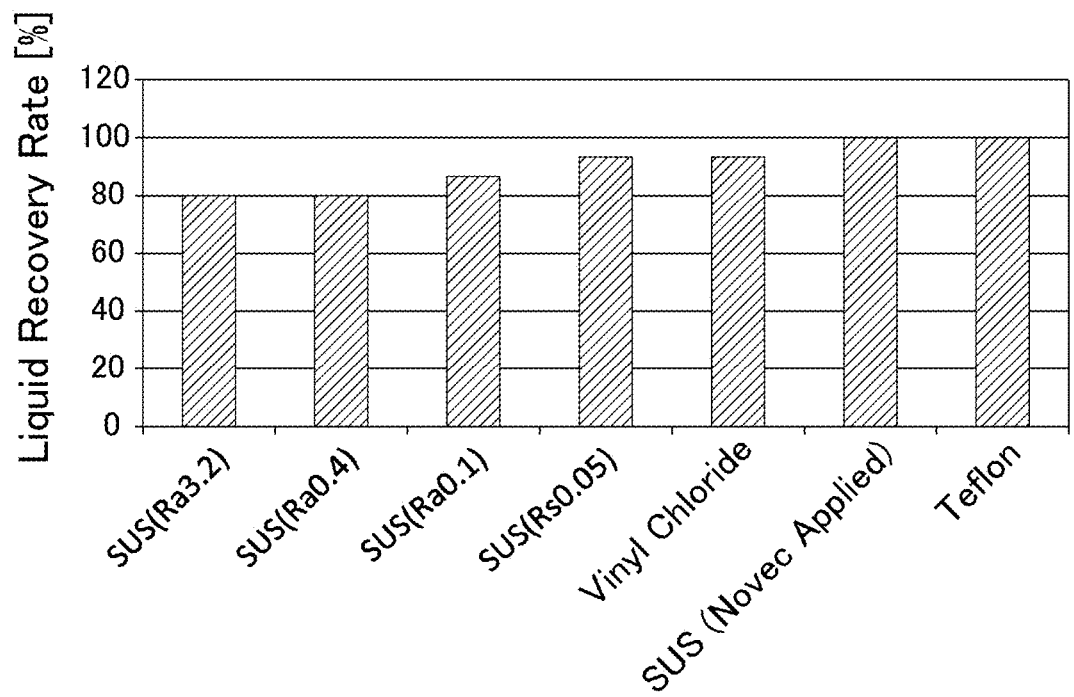
FIG. 15 is a diagram showing a result obtained by evaluating a difference in a liquid recovery rate derived from a material of piping.

FIG. 15 is a diagram showing a result obtained by evaluating a difference in a liquid recovery rate derived from a material of piping. In FIG. 15, the ordinate represents a recovery rate, and the abscissa represents a material. Evaluation was made with respect to a pipe of each material under condition that the number of pipes is one, and a flow rate is 2.5 ml/min (equivalent to 20 ml/min for eight pipes).

In FIG. 15, SUS (Ra 3.2) shown on the leftmost side represents piping used in the experiment shown in FIG. 14 and indicated a recovery rate as low as 80%. In the experiment using a Teflon (registered trademark) tube shown in the rightmost side obtained a recovery rate of 100%.

A difference between a common SUS tube and a Teflon (registered trademark) tube resides in wettability and surface roughness. Teflon (registered trademark) has excellent water-repellent and poor wettability. SUS has excellent wettability. Additionally, SUS has a coarse surface, which is approximately Ra 3.2. An extracting tube made of Teflon (registered trademark) has Ra of approximately 0.02.

Experiment results in which a coating agent Novec manufactured by 3M with excellent wettability was applied to an inner surface of a SUS tube, and experiment results using a tube made of vinyl chloride with excellent wettability showed high recovery rates. From these results, higher wettability of a SUS itself does not matter and is considered not to cause a reduction in a recovery rate at a low flow rate. Additionally, as a result of abrading the inner surface of the same SUS tube to increase smoothness, Ra, such as 0.4, 0.1, and 0.05, a liquid recovery rate was significantly improved. It is considered that when a fluid has a low velocity, droplets scatter together with $CO_2$ to disappear due to a structure with the coarse inner surface of the flow channel.

From the foregoing results, the cause of a reduction in a liquid recovery rate when a flow rate was low in FIG. 14 is considered to be smoothness of the inner surface of the tube. Additionally, it is considered that a high liquid recovery rate can be obtained even in a low flow rate region by setting the inner surface of the flow channel after being branched to have smoothness Ra of approximately 0.05 or less.

The experiment results shown in FIG. 14 is a result obtained when a temperature of a mobile phase immediately before being introduced into the gas-liquid separator was maintained at 10° C. In the super-critical fluid device, a mobile phase is ordinarily heated at 40° C. or more in order to bring a fluid passing through a column or an extraction container into a super-critical state.

However, when a mobile phase has a high temperature, dissipation due to evaporation of a modifier decreases a recovery rate. Thus, a mobile phase to be introduced into the gas-liquid separator preferably has a low temperature.

Figure 16:
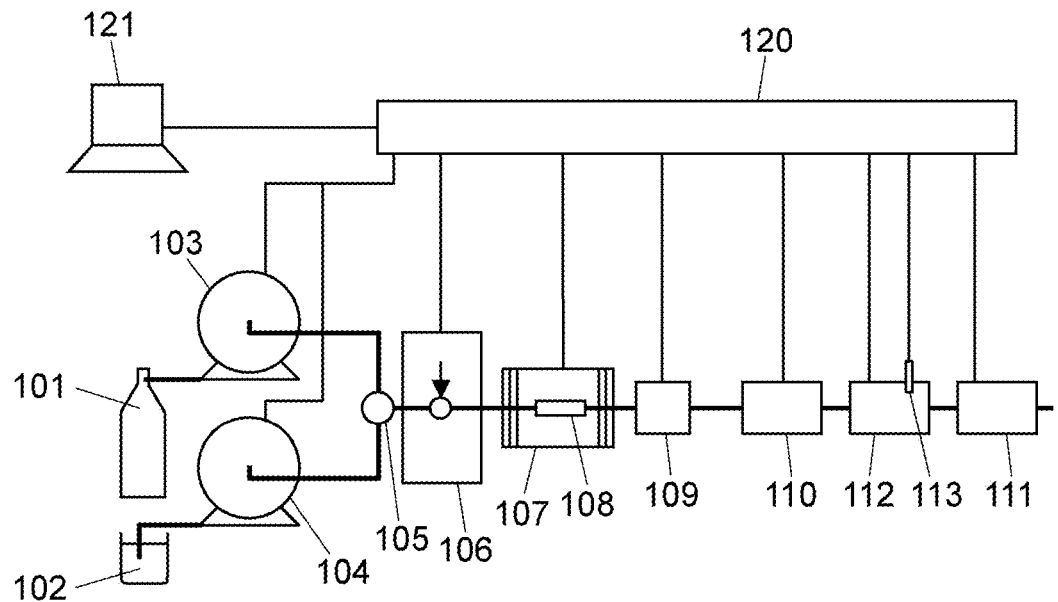
FIG. 16 is a schematic view of a configuration for explaining another embodiment of a super-critical fluid device.

FIG. 16 is a schematic view of a configuration for explaining another embodiment of a super-critical fluid device.

As compared with the configuration shown in FIG. 2, the super-critical fluid device of this embodiment additionally includes a cooler 112, a temperature detector 113, a system controller 120 (control unit), and a monitor 121. The temperature detector 113 detects a temperature of the cooler 112.

Although not essential for operation of a SFC, the system controller 120 is ordinarily provided for conducting various automatic operations. Preparation for the system made by the system controller 120 will be described with reference to the flow chart of FIG. 17. The preparation for the system here represents operation conducted before the automatic sampler 106 enters an allowable state for injection of a sample to be dispensed.

Figure 17:
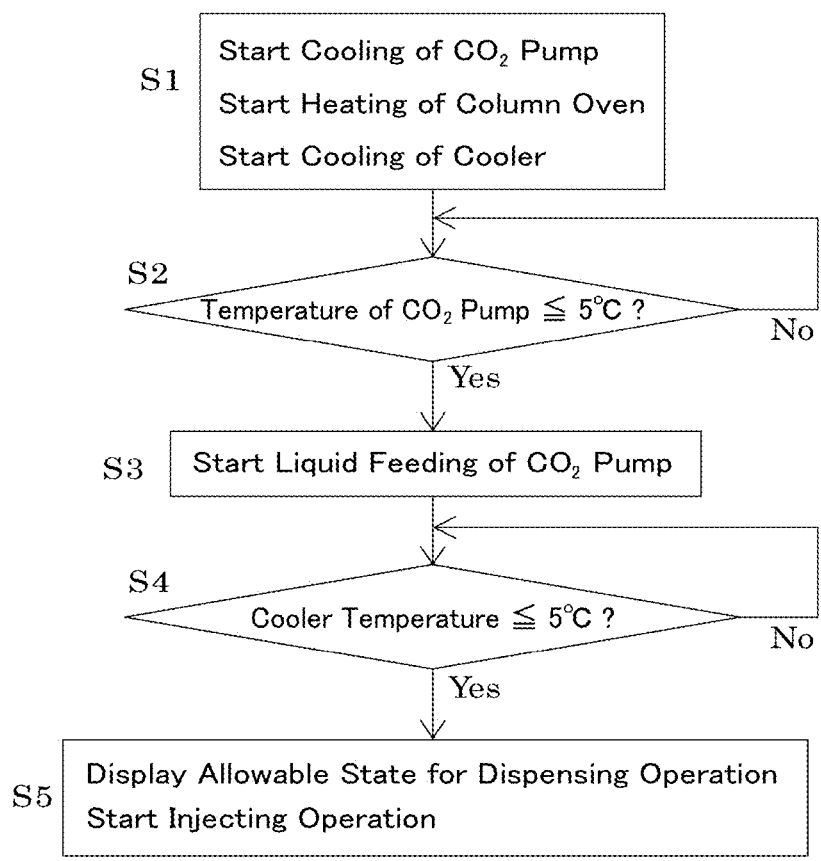
FIG. 17 is a flow chart for explaining system preparation operation of the super-critical fluid device.

FIG. 17 is a flow chart for explaining system preparation operation of the super-critical fluid device.

The system controller 120 first conducts cooling of the $CO_2$ pump 103, heating of the column oven 107, and cooling of the cooler 112 (Step S1).

Using a temperature detector not shown, the system controller 120 determines whether a temperature of the $CO_2$ pump 103 is satisfactorily reduced or not (Step S2).

After the temperature of the $CO_2$ pump 103 becomes a specified value (e.g. 5° C.) or below, the system controller 120 causes the $CO_2$ pump 103 and the modifier pump 104 to operate to start feeding $CO_2$ and a modifier (Step S3).

The system controller 120 monitors a temperature of the cooler 112 by using the temperature detector 113 to determine whether the temperature detected by the temperature detector 113 becomes lower than the specified value (e.g. 5° C.)(Step S4).

When determining that the temperature of the cooler 112 becomes lower than the specified value, the system controller 120 starts sample injecting operation by the automatic sampler 106 (Step S5). At Step S5, other than the start of the injecting operation, the system controller 120 may cause the monitor 121 to display an allowable state for dispensing operation, or cause display indicators of the system controller 120, the cooler 112, and the fraction collector 111 to light, or conduct these operations in combination.

In the super-critical fluid device shown in FIG. 17, a temperature detector may be provided which detects a temperature of a gas-liquid separator in the fraction collector 111. Additionally, a gas-liquid separator may be provided in a flow channel between the cooler 112 and the fraction collector 111, and a temperature detector which detects a temperature of the gas-liquid separator may be provided. Additionally, a temperature detector may be provided which detects a temperature of a mobile phase immediately before being introduced into the gas-liquid separator. Such a temperature detector is arranged, for example, at a position for detecting a temperature of a flow channel between the cooler 112 and the gas-liquid separator. Upon determining that a result of monitoring of a temperature detected by these temperature detectors becomes a specified value or below, the system controller 120 causes the automatic sampler 106 to operate.

Figure 18:
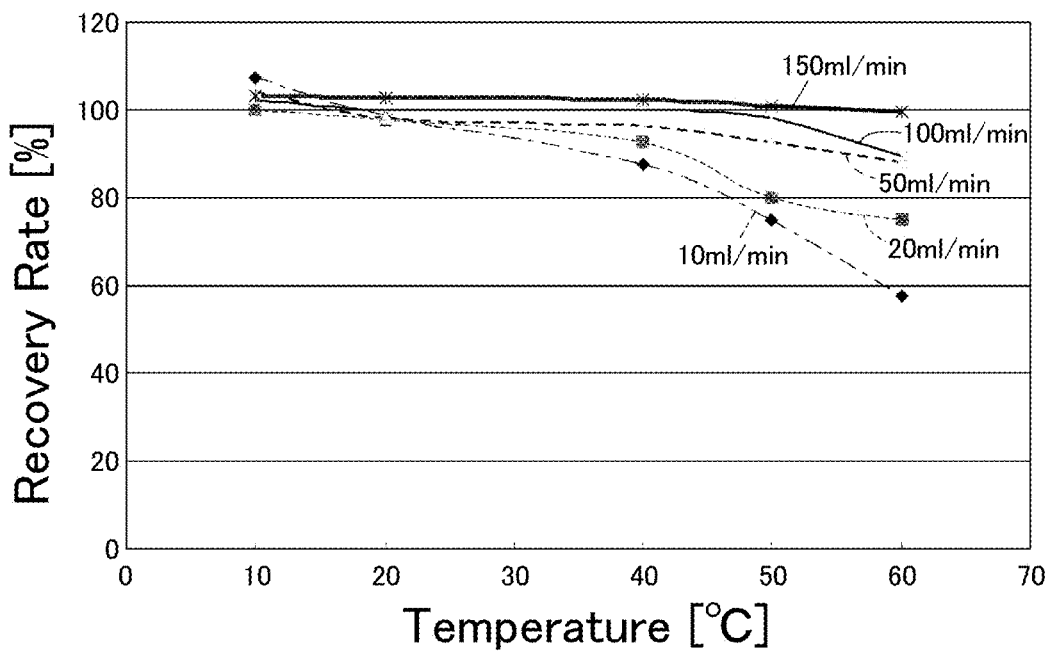
FIG. 18 is a diagram showing experiment results which verified a cooling effect of a mobile phase.

FIG. 18 is a diagram showing experiment results which verified a cooling effect of a mobile phase. In FIG. 18, the ordinate represents a liquid recovery rate, and the abscissa represents a temperature of a mobile phase. These experiment results is a result obtained not with the branched piping system shown in FIG. 13 but with a tube connected which has an internal diameter of 6 mm and a length of 15 cm to expand a cross section of a flow channel with ease. However, the results can be used as a result showing a relationship between a temperature and a liquid recovery rate.

With a flow rate of $CO_2$ containing 20% methanol as a modifier set to be 10 ml/min, 20 ml/min, 50 ml/min, 100 ml/min, and 150 ml/min, respectively, a recovery rate of methanol with a temperature set to be 10 C.° to 60 C.° was obtained at each flow rate.

When the set temperature of the cooler 112 was 10 C.°, the methanol recovery rate of 100% was obtained in all the conditions for a flow rate. As the set temperature increased, the recovery rate decreased. It is found that in a case of a high flow rate, as compared with a case of a low flow rate, a rate of reduction in the recovery rate is lower to be less affected by a set temperature of the cooler 112.

When the flow rate of $CO_2$ is high, a fluid is actively cooled due to evaporation heat following vaporization of $CO_2$ and adiabatic expansion. Accordingly, it is considered that similarly to a case using a cooler, evaporation of methanol was satisfactorily suppressed to increase a recovery rate.

From the foregoing result, it has been confirmed that when a flow rate of $CO_2$ is relatively high (e.g. 50 ml/min to 150 ml/min), a cooling effect due to evaporation heat of $CO_2$ and adiabatic expansion enables evaporation of a modifier to be suppressed, thereby enabling improvement in a sample recovery rate.

By contrast, when a flow rate of $CO_2$ is relatively low (e.g. 5 ml/min to 50 ml/min), forced cooling is effective which uses a Peltier device, a low temperature or high temperature water tank, or the like in the cooler 112. Other than forced cooling means, instantaneous vaporization of $CO_2$ in a short distance by using an orifice or the like obtains a relatively large cooling effect to realize a cooler replacing forced cooling.

Figure 19:
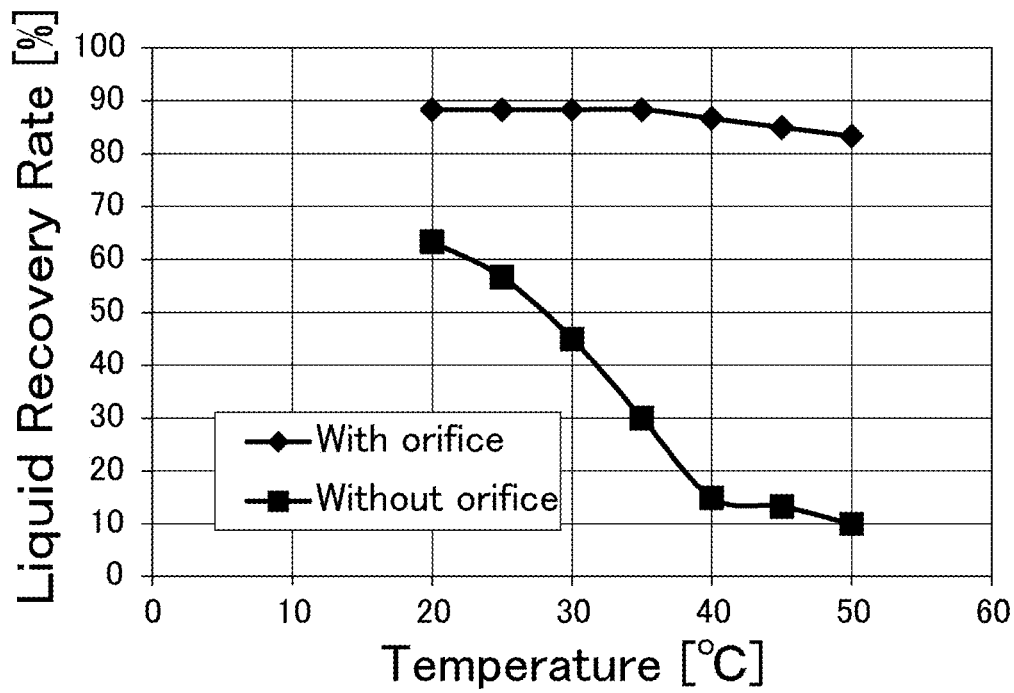
FIG. 19 is a diagram showing a result obtained by evaluating temperature dependencies of a liquid recovery rate which was obtained when an orifice is disposed immediately before the gas-liquid separator and which was obtained when the same is not arranged.

FIG. 19 is a diagram showing a result obtained by evaluating temperature dependencies of a liquid recovery rate which was obtained when an orifice is disposed immediately before the gas-liquid separator and which was obtained when the same is not arranged. In FIG. 19, the ordinate represents a liquid recovery rate and the abscissa represents a temperature.

With a flow rate of methanol set to be 1 ml/min and a flow rate of $CO_2$ set to be 4 ml/min, a recovery rate of methanol flowing out was evaluated. Evaluation was made of a dependency of a liquid recovery rate on a set-temperature of the cooler 112 in a case where the cooler 112 and the fraction collector 111 had nothing provided therebetween, and a case where an orifice having an opening with an internal diameter of 50 μm (micrometer) was provided.

Without an orifice, while at a temperature of 20° C., the methanol recovery rate was 63%, as the set temperature increased, the methanol recovery rate gradually decreased, and at the set temperature of 50° C., the obtained recovery rate was only 10%. By contrast, with an orifice, the recovery rate was constantly 90% without depending on a temperature. From such results, it has been confirmed that a recovery rate of a modifier can be improved by using a cooling effect attained by instantaneously vaporizing $CO_2$ using an orifice even without forcedly cooling a temperature of a fluid.

The cooler using an orifice is arranged at a position, for example, of the cooler 112 in FIG. 16. The orifice is better provided as a cooler at a connection portion between piping from the pressure control valve 110 and piping leading to the fraction collector 111.

Figure 20:
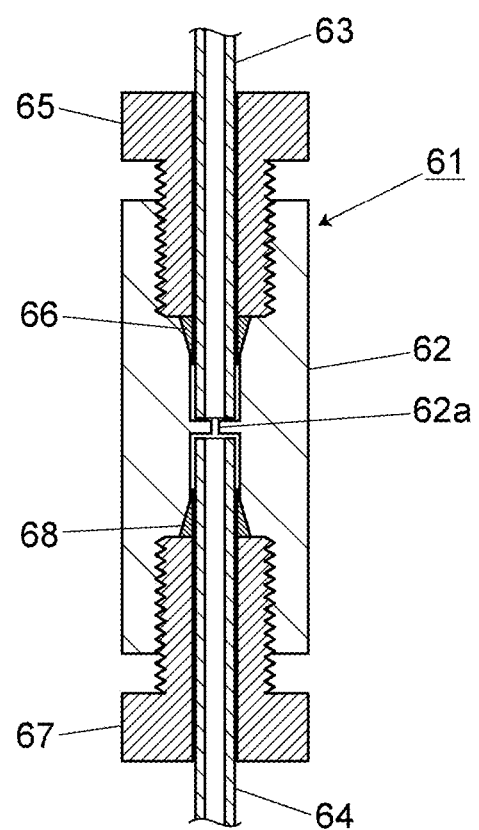
FIG. 20 is a schematic sectional view for explaining one example of a cooler having an orifice.

FIG. 20 is a schematic sectional view for explaining one example of a cooler having an orifice.

A cooler 61 includes a joint 62 having an orifice 62a. An inlet tube 63 and an outlet tube 64 are connected via the joint 62. The inlet tube 63 is connected to the joint 62 by a male nut 65 and a ferrule 66. The outlet tube 64 is connected to the joint 62 by a male nut 67 and a ferrule 68.

In the joint 62, the orifice 62a is arranged between an end portion of the inlet tube 63 and an end portion of the outlet tube 64. An internal diameter of the orifice 62a is smaller than an internal diameter of the inlet tube 63 and an internal diameter of the outlet tube 64. The orifice 62a reduces an internal diameter of a flow channel for a mobile phase.

An end portion of the inlet tube 63 opposite to the joint 62 is connected to, for example, a back pressure regulator. An end portion of the outlet tube 64 opposite to the joint 62 is connected to, for example, a gas-liquid separator.

When a mobile phase (e.g. super-critical $CO_2$+a modifier) flows to the cooler 61, $CO_2$ is instantaneously vaporized in a short distance by the orifice 62a, thereby cooling a mobile phase (gas-liquid mixed fluid) containing gas $CO_2$.

Although in the foregoing, the embodiments of the present invention have been described, the configurations, the structures, and the numerical values in the embodiments are illustrative only, and the present invention is not limited thereto, and various modifications can be devised without departing from the scope of the invention as recited in the Scope of Claims for Patent.

DESCRIPTION OF REFERENCE SIGNS

1, 10, 11, 12, 402: gas-liquid separator
2, 402a: inlet tube (introduction flow channel)
4, 41, 51a, 402b: discharge flow channel
4a, 41a, 51b: discharge port
5, 402c: liquid inducing column (liquid collecting member)
51: liquid collecting member
61, 112: cooler
62a: orifice
103, 104: pump
106: automatic sampler (sample injector)
108: column
109: detector
110: pressure control valve (back pressure regulator)
112: cooler
113: temperature detector
120: control unit

The invention claimed is:

1. A gas-liquid separator that separates a mobile phase containing a gas and a liquid into a gas and a liquid, the gas-liquid separator comprising:
    an introduction flow channel to which a mobile phase is introduced; and
    a plurality of discharge flow channels connected to the introduction flow channel,
    wherein from a discharge port of the plurality discharge flow channels, discharges a gas and a liquid and separates the gas and the liquid after discharge; and
    further comprising a liquid collecting member having an outer wall surface on which a liquid discharged from the discharge port of the discharge flow channel moves while being adhered thereto.

2. The gas-liquid separator according to claim 1, wherein the liquid collecting member has a cylindrical shape or a cone shape.

3. The gas-liquid separator according to claim 1, wherein at least a part of the discharge flow channel is formed within the liquid collecting member, and
    the discharge port of the discharge flow channel is formed on the outer wall surface of the liquid collecting member.

4. The gas-liquid separator according to claim 1, wherein an internal diameter of the discharge flow channel is 2 mm or less.

5. The gas-liquid separator according to claim 1, wherein the discharge flow channel is vertically arranged.

6. A super-critical fluid device comprising a pump, a back pressure regulator, and the gas-liquid separator according to claim 1, wherein
    a mobile phase containing a liquid and a super-critical fluid or a liquefied gas is fed by the pump, and a mobile phase having passed through the back pressure regulator is introduced into the gas-liquid separator.

7. The super-critical fluid device according to claim 6, wherein between the back pressure regulator and the gas-liquid separator, a cooler is connected.

8. The super-critical fluid device according to claim 7, wherein the cooler has an orifice.

9. The super-critical fluid device according to claim 7, further comprising:
   a sample injector connected between the pump and the back pressure regulator;
   a column connected between the sample injector and the back pressure regulator; and
   a detector connected between the column and the back pressure regulator.

10. The super-critical fluid device according to claim 9, further comprising:
    a temperature detector for detecting a temperature of a mobile phase immediately before being introduced into the gas-liquid separator, a temperature of the cooler, or a temperature of the gas-liquid separator; and
    a control unit which causes the sample injector to operate upon determining that a result of monitoring of a temperature detected by the temperature detector becomes a specified value or below.

\* \* \* \* \*